United States Patent [19]

Bartholomew et al.

[11] 4,232,683

[45] Nov. 11, 1980

[54] THERAPEUTIC INCENTIVE SPIROMETER

[75] Inventors: Victor L. Bartholomew, Hemet, Calif.; Harold R. Havstad, Eagle Point, Oreg.

[73] Assignee: Hudson Oxygen Therapy Sales Company, Temecula, Calif.

[21] Appl. No.: 924,919

[22] Filed: Jul. 17, 1978

[51] Int. Cl.³ .................... A61B 5/08; A63B 23/00
[52] U.S. Cl. ...................................... 128/725; 272/99
[58] Field of Search ............ 128/716, 718, 720, 725, 128/726, 727, 728, 188, 202, 145.8, 208; 272/99

[56] References Cited

U.S. PATENT DOCUMENTS

| 3,785,377 | 1/1974 | Jorgensen | 128/188 |
| 3,898,987 | 8/1975 | Elam | 128/145.8 |
| 4,025,070 | 5/1977 | McGill et al. | 272/99 |

Primary Examiner—Henry J. Recla
Attorney, Agent, or Firm—Seiler & Quirk

[57] ABSTRACT

A therapeutic incentive spirometer comprises a spirometer body having an outer wall and an inner wall, separated by a passageway, an interior chamber defined by said inner wall, a gas outlet for directing gas out of the chamber, a gas inlet means for directing gas into the chamber. A component for varying the flow rate of gas through either the gas inlet or outlet, and visual device associated with the interior chamber for indicating the rate of gas flow through the chamber. The preferred device includes a cap having a gas by-pass intake port located therein, which port is registered with a slanted surface on the outer body wall, the cap being movable relative to the body wall which movement changes the by-pass port opening size.

21 Claims, 12 Drawing Figures

THERAPEUTIC INCENTIVE SPIROMETER

BACKGROUND OF THE INVENTION

Devices for measuring lung volume capacity and for exercising the lungs through breathing exercises have been known for some time. Examples of such devices are shown in U.S. Pat. Nos. 393,869, 515,637, 793,177, 1,926,748, 2,100,898 and 3,695,608. The devices disclosed in the aforesaid patents are operated by the patient or user forcing air out of the lungs into the device. Breath control or lung exercise is achieved by varying the resistance to discharge of the air through the device.

More recently, it has been observed that for patients suffering from diseases which restrict the lung volume capacity, such as bronchitis, emphysema, and the like, and for a condition known as atelectasis, lung volume capacity is best expanded by exercises in which a patient inhales, rather than exhales, as taught in the aforesaid prior art. Moreover, for increasing patient exercise incentive, a device preferably incorporates visual means for the patient to observe success or achievement during the exercise, and means for varying the difficulty of the exercise. It is to such a device that the present invention is directed.

SUMMARY OF THE INVENTION

The device of the present invention comprises a lung volume exercising apparatus, or incentive spirometer, comprising an inner and outer wall separated by a gas passageway, the inner wall defining an interior chamber, in which is received a lightweight object, such as a ball, which normally lies gravitationally at the bottom of the chamber. The passageway between the inner and outer walls communicates with both the interior chamber and a gas outlet port, to which is connected a tubing or the like, and a mouthpiece, which is placed in a user's mouth. The device also includes a gas inlet means for directing gas into the interior chamber in response to a user inspiring gas through the mouthpiece, tubing, and gas outlet port, which concomitantly causes gas to be directed through the inlet means to the chamber, whereupon the ball or other visual means is visably moved from its normal rest position. Means is also provided for varying the difficulty of the exercise, comprising varying the size of a by-pass port opening which directs gas to the passage during user inspiration. These as well as other features of the device and its uses will be evident from the following detailed description.

DETAILED DESCRIPTION OF THE INVENTION

Figure 1:
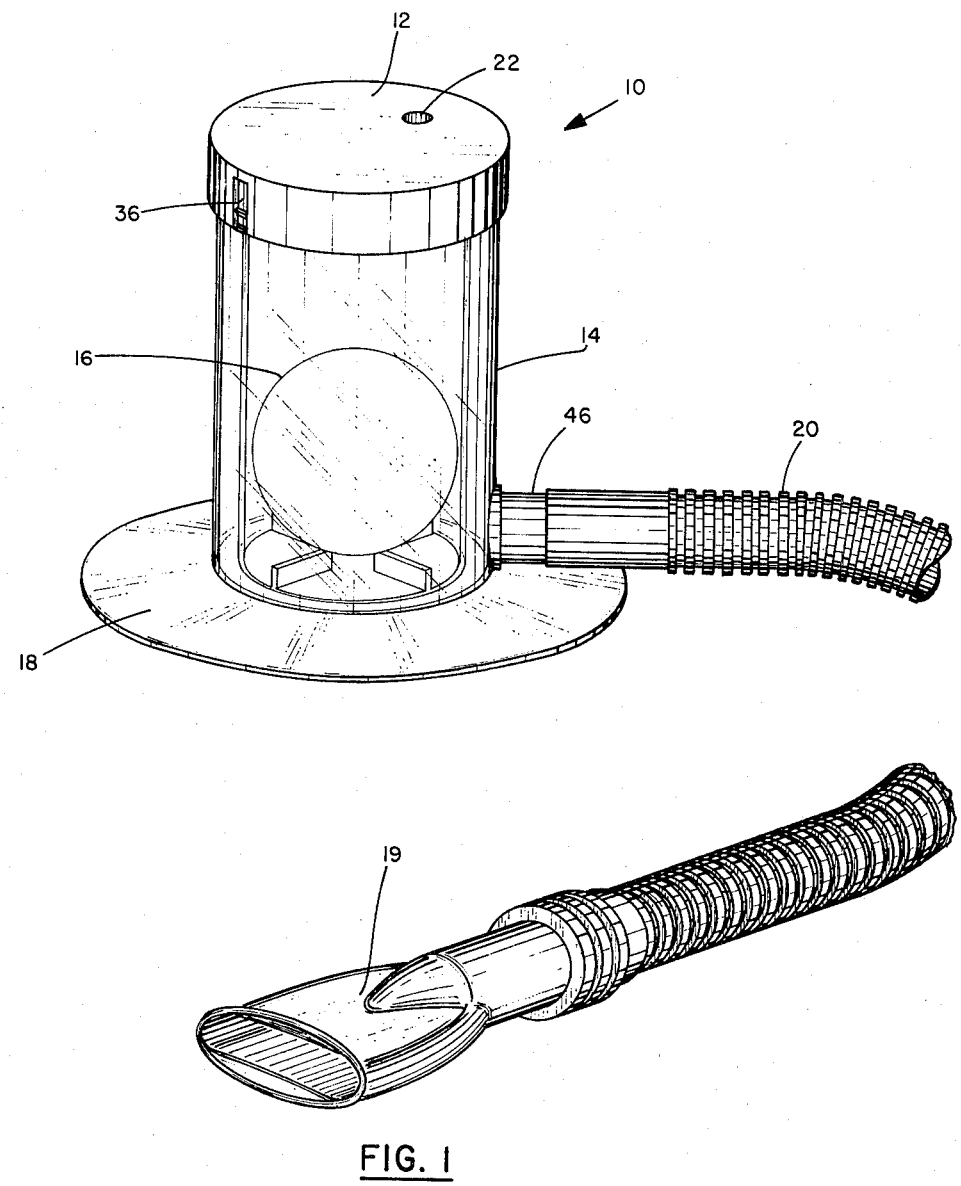
FIG. 1 is a perspective view showing a preferred incentive spirometer device according to the invention.
Figure 2:
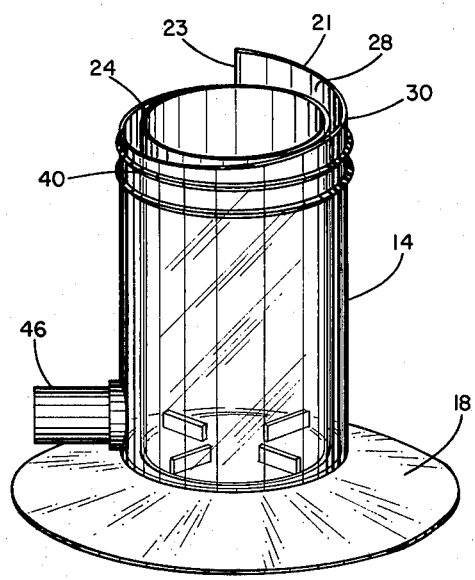
FIG. 2 is an illustration of one embodiment of a spirometer body with the cap removed.

In FIG. 1 there is illustrated the incentive spirometer 10 which includes a spirometer body 14, a cap, rotatably movable relative to the body, which cap has a gas inlet port 22, a base 18, on which spirometer body 14 is secured, a gas outlet pipe 46, and tubing 20 secured between the outlet pipe and mouthpiece 19. A lightweight ball 16, such as a ping pong ball or foamed plastic, is disposed in an interior chamber in the spirometer body 14. When a user, with mouthpiece 19 inserted in his or her mouth, inhales, gas is drawn through gas outlet pipe 46 and into the interior chamber via gas inlet port 22, causing ball 16 to rise, which can be visually detected by the user. Thus, spirometer body 14 is preferably at a comfortable user eye level so that the rising of ball 16 can be easily observed. As will be further explained, the difficulty of the exercise can be varied by rotating cap 12 relative to spirometer body 14, whereby the size of by-pass port 36 opening is varied.

One embodiment of the invention is illustrated in the drawings of FIGS. 2–4 and 6–8. In this embodiment, the spirometer body comprises an exterior or outer wall 30, and an inner wall 24, separated by a gas passageway 28, which forms a suction chamber. A first gas outlet port 48 communicates with gas passageway 28, and exteriorly of the device, through gas outlet pipe 46. A second gas outlet port 34 communicates with interior chamber 26 and gas passageway 28. As shown, both outer and inner spirometer body walls 30 and 24, respectively, are annular, and interior chamber 26 is cylindrical and somewhat elongated so as to provide sufficient space for a lightweight visible means, such as ball 16, to be displaced in a manner which can be visibly detected by an observer.

Figure 4:
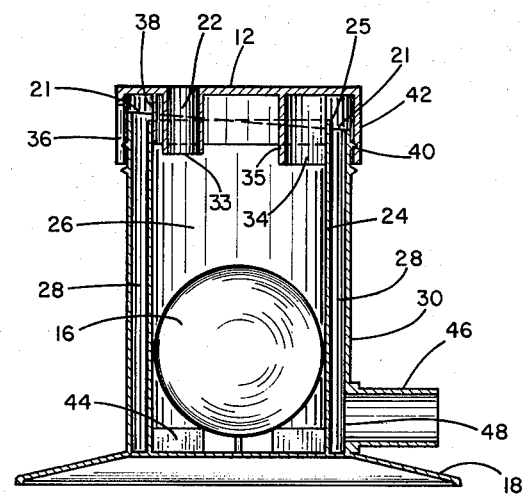
FIG. 4 is a sectional elevation of a spirometer according to the invention.
Figure 5:
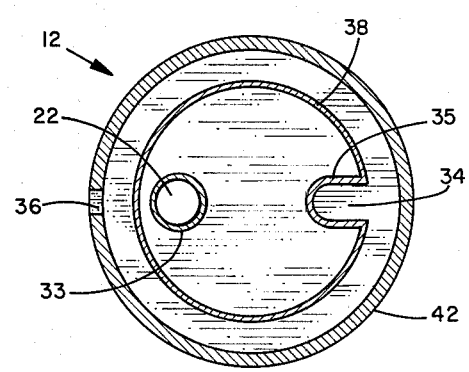
FIG. 5 is a plan view of the inside of the cap of the type shown in FIG. 4.

In FIG. 5, there is shown a cap 12 for being secured on the top of the spirometer body in a manner illustrated, for example, in FIGS. 1 and 4. The cap thus overlies gas passageway 28 and interior chamber 26. Moreover, the cap is preferably designed, whereby the outer annular side 42 of the cap, extends downwardly beyond the outer wall 30, and sealingly engages the wall, to prevent substantial gas leakage. For that purpose, a sealing ring 40, is conveniently molded into the outer spirometer body wall, as shown, or on the interior surface of the cap sidewall 42.

In the preferred embodiment, the cap is provided with a gas inlet port 22, which port extends through the upper cap surface, and is further defined by an annular inlet port wall 33. The gas inlet port wall is for the purpose of defining a tunnel or tubelike structure for directing a stream of gas downwardly into interior chamber 26 from port 22. It will also be mentioned here that since it is a desirable function of the device to cause ball 16 to rise or be floated upwardly within the interior chamber, this is best accomplished with gas inlet port 22 and inlet port wall 33 being offset from the cap center somewhat so as to direct the incoming gas downwardly within interior chamber 26 to the side of the ball, rather than directly on the center of the ball. It will be understood that since it is desirable for the ball to rise, it will do so more effectively if the gas inlet port is offset.

The device also includes an outlet port communicating between chamber 26 and passageway 28. Such an outlet port may be conveniently provided on the cap. Thus, cap 12 also includes an outlet port 34 formed by inwardly extending outlet port wall 35, which wall is contiguous with a cap ring 38. Preferably, the annular cap ring 38 will be positioned, and of a diameter, so that it extends downwardly to contact interior wall 24, thereby providing some gas sealing engagement therewith. The outlet port wall 35 extends inwardly from interior wall 24 to fully expose port 34 to both gas passageway 28 and interior chamber 26. Finally, a by-pass port 36 is also formed on the cap. Instead of securing interior wall 24 to base member 18 as shown in FIG. 4, the device may be constructed with the interior wall secured to the cap and having the bottom of the interior chamber closed with a base plate of the like, so that the interior wall and chamber are rotated with the cap relative to the outer wall. The interior wall may be conveniently snap or press-fit to the cap to provide access to the interior chamber, for example, where the parts are seperately formed. Otherwise such a device functions substantially as described hereinafter.

Figure 3:
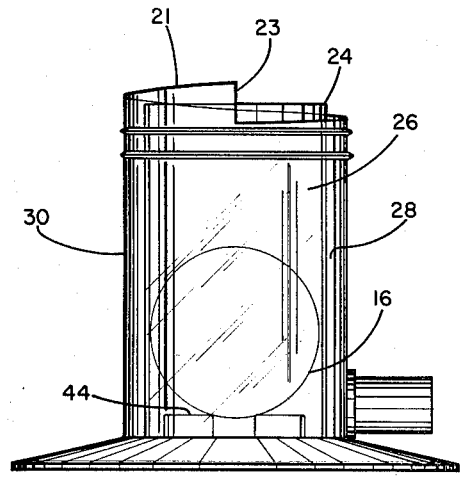
FIG. 3 is an elevational view of the spirometer body of FIG. 2, viewed from the other side.

In using the device, as the user inhales through mouthpiece 19, suction is created in gas passageway 28, and gas is concomitantly introduced into interior chamber 26 from gas inlet port 22, thereby causing ball 16 to rise. The gas is directed from the interior chamber through outlet port 34, along passageway 28, and finally exits through outlet port 48. Once the rate of gas flow through the chamber is sufficient to lift the ball from its rest position, the ball rises. For any given ball weight, a certain minimum flow rate will be required to lift the ball to the top of the chamber, where it will remain so long as that or a greater gas flow rate is maintained. If by-pass port 36 is closed, all of the gas inhaled by the user through the device passes through inlet port 22 thereby making the exercise relatively easy. Difficulty in a breathing exercise using the device is created by allowing some of the gas inhaled by the user to be introduced through by-pass port 36. In order to gradually expose or open more of by-pass port 36, outer spirometer body wall 30 is provided with a slanted upper surface 21, which preferably slants in a helical manner from edge 23, as shown in FIG. 3. Helical surface 21 is at its highest and lowest relative to the bottom of the device at edge 23. It is this helical surface which is used to determine the size of the opening of by-pass port 36. Thus, as cap 12 is rotated relative to spirometer body 12, the by-pass port opening exposed between port 36 and helical surface 21 is changed to vary the difficulty of the exercise, as will be explained further hereinafter. For user or operator assistance, it may be desirable to include indica on the device for designating flow rates at different cap positions. For example, flow rates may be stamped on either the cap or outer wall surface with an opposing index marking.

Figure 6:
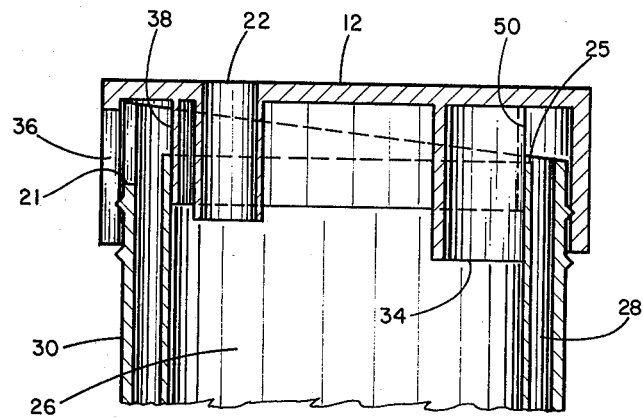
FIGS. 6–8 are sectional views of the upper portion of a spirometer embodiment illustrated in FIG. 2, showing different positions of a cap relative to the spirometer body, for varying exercise difficulty.
Figure 7:
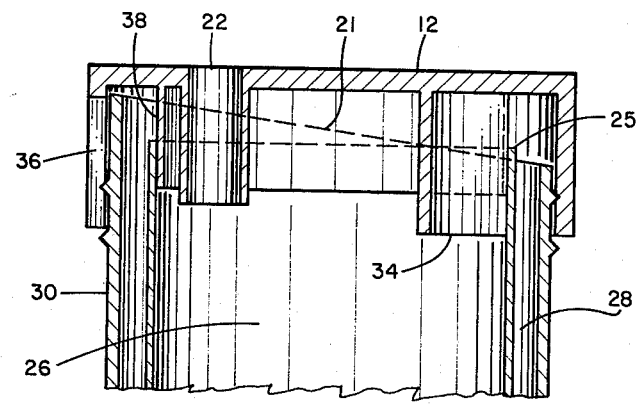
Figure 8:
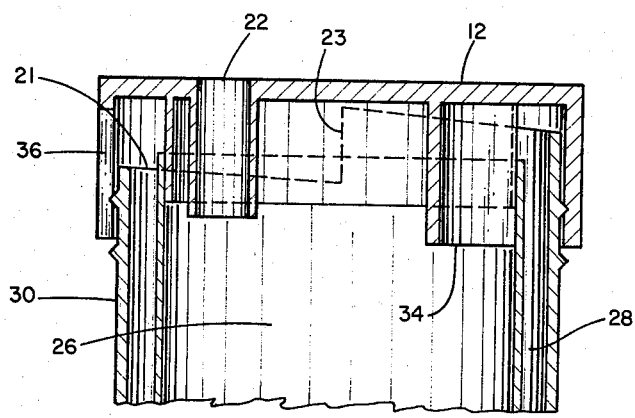

The operation of the spirometer device is further understood by reference to FIGS. 6-8, in addition to FIG. 4. As previously explained, with the user inhaling through the device via mouthpiece 19, tube 20 (FIG. 1), gas is drawn into interior chamber 26 via inlet port 22, where it is directed downwardly by inlet port wall 33 alongside ball 16. The ball is preferably lightweight, such as a ping pong ball, or the like, whereby the minimum gas flow rate required to raise the ball are relatively low, especially where the users have significantly reduced lung capacities. The ball may be held off of the interior chamber floor by standoff ribs 14, which allow gas to pass beneath the ball. As the incoming gas is then drawn outwardly through outlet port 34, over interior wall upper edge 25, and into gas passageway 28, ball 16 rises. This upward ball displacement is readily observed by the user and indicates successful accomplishment of that portion of the exercise.

The exercise is most easily accomplished with by-pass port 36 closed. This disposition of the apparatus is achieved by turning cap 12 relative to the spirometer body until upper helical surface 21 of the outer wall 30 extends above by-pass port 36, thereby fully occluding or covering the port as shown in FIG. 7. With the by-pass port opening 36 closed, substantially all of the gas passing through the device is introduced via gas inlet port 22, so that the full inhalation effort of the user causes the ball to rise. Where more difficulty in the exercise is desired, cap 12 is rotated relative to the spirometer body, whereby more and more of by-pass port 36 is exposed by the gradually descending helical surface exposure 21. For example, observing FIG. 8, cap 12 has been rotated so that helical surface 21 covers approximately half of the by-pass port 36. In such a position, with a portion of by-pass port 36 exposed, some of the air inhaled by the patient and drawn through the device, is introduced through the by-pass port. Accordingly, for any given inhalation effort by a user, with some of the gas satisfying that effort passing through the device via by-pass port 36, the flow of gas into interior chamber 26 via gas inlet port 22 is correspondingly reduced, and the effort required to raise the ball within interior chamber 26 is increased.

FIG. 6 shows the apparatus in a still more difficult exercise condition, with cap 12 rotated to expose even more of by-pass port 36. In that condition, it will be understood that for any given inhalation effort of a user, there will be a greater flow rate of gas passing through the by-pass port, as compared to either condition shown in FIG. 7 or FIG. 8. Concomitantly, as the gas flow through the by-pass port increases, the flow through inlet port 22 decreases, and the effort required to raise the ball increases. With surface 21 sloping gradually, the exercise difficulty is gradually increased or decreased by rotating the cap. However, the surface may instead be stair-stepped, or notched, or otherwise formed so that by-pass port openings are more markedly varied as the cap is rotated. For example, the outer wall may be provided with a series of orifices of different sizes, which may be successively registered with the by-pass port by rotating the cap. Each orifice will correspond to a certain flow rate, which may be marked or indexed on the device for more easily determining the exercise difficulty setting.

Figure 9:
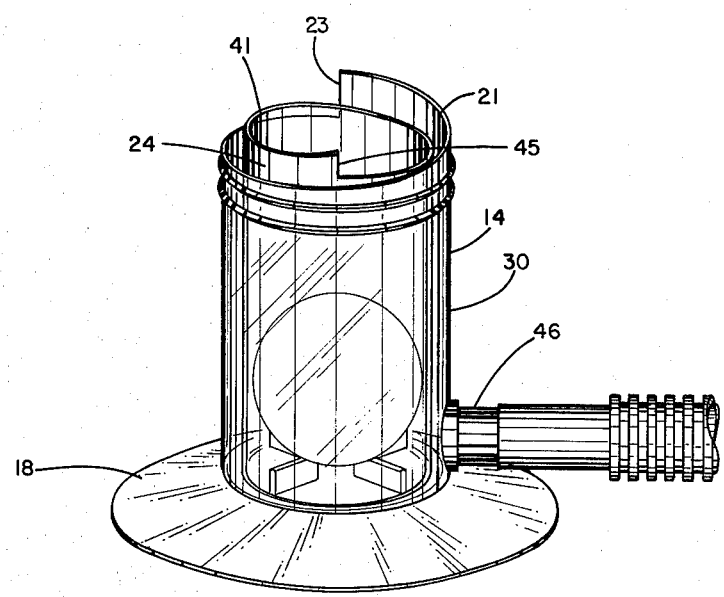
FIG. 9 is a perspective view illustrating another embodiment of a spirometer body, with the cap removed.
Figure 10:
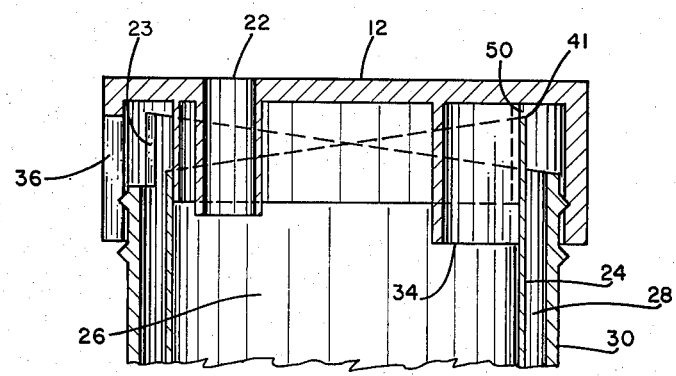
FIGS. 10 and 11 are sectional elevations of the top portion of the spirometer body embodiment of FIG. 9, showing different cap positions relative to the spirometer body for varying exercise difficulty.
Figure 11:
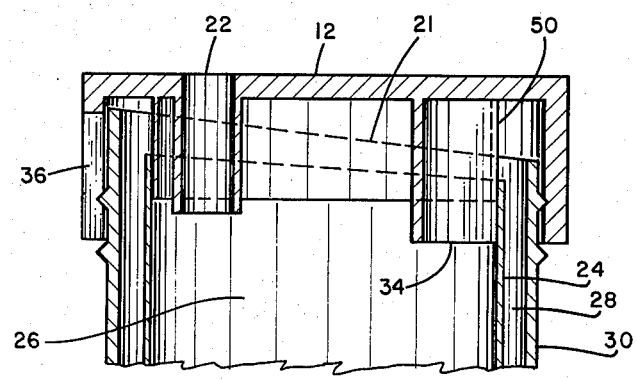

A further and alternative embodiment of the apparatus is illustrated in FIGS. 9-11 in which the upper surface 41 of inner wall 24 is also a helical surface, gradually tapering from edge 45. By providing such an upper helical surface 41 for the interior spirometer body wall, additional difficulty variation in accomplishing the breathing exercise through the device is provided. Using such a feature, not only is the exposure or opening of by-pass port 36 varied by rotating cap 12 relative to the spirometer body, but the opening of gas outlet port 34 is also varied. Thus, the difficulty of the breathing exercise utilizing the invention shown in FIGS. 9-11 is determined by the disposition of both helical surfaces 21 and 41 of the outer and interior walls 30 and 24, respectively. It will be noted that helical surface 21 slants downwardly from edge 23 while surface 41 slants downwardly from edge 45, the edges being on opposite sides of the spirometer body. Using the device of this embodiment, and incorporating cap 12 having the same design as illustrated in FIG. 5, relatively difficult and easy exercises are accomplished in the cap positions shown in FIGS. 10 and 11, respectively.

FIG. 10 shows cap 12 in a position relative to spirometer body whereby by-pass port 36 is fully open, which, as previously explained, will make the breathing exercise more difficult, in requiring more breathing effort (flow rate) to raise the ball within interior chamber 26. However, in this embodiment, not only is the by-pass port open, but the passage of gas through channel 50 is restricted due to the proximity of upper helical surface 41 of inner wall 24, relative to the underside of cap 12. Comparison of channel 50 in both FIGS. 10 and 6 further illustrates the difference between the single and double helix embodiments. FIG. 11 shows the double helix embodiment in the easy exercise position, with by-pass port 36 being closed, whereby substantially all of the gas pulled through the device by the inhaling patient or user is directed through gas inlet port 22. Thus, gas flow rates through the chamber are readily increased for more easily raising the ball in interior chamber 26. Moreover, the relatively large channel 50 for directing gas from outlet port 34 to passageway 28 will be noted.

Although the double helix embodiment is shown with the edges 45 and 23 of the inner and outer wall surfaces, respectively, being opposite one another, the device may be modified so that these edges are on the same side of the spirometer body. In that event, it may be further desirable to modify the cap whereby by-pass port 36 and outlet port 34 are located on the same side of the cap. It will also be desirable to place the gas inlet port on the opposite side of the cap. Although the double helix embodiment thus offers a greater variation in exercise difficulty, an advantage of the single helix embodiment shown in FIGS. 2-4 and 6-8 is a more constant pressure through all cap positions, since channel 50, through which gas from the interior chamber passes into passageway 28, remains constant.

Figure 12:
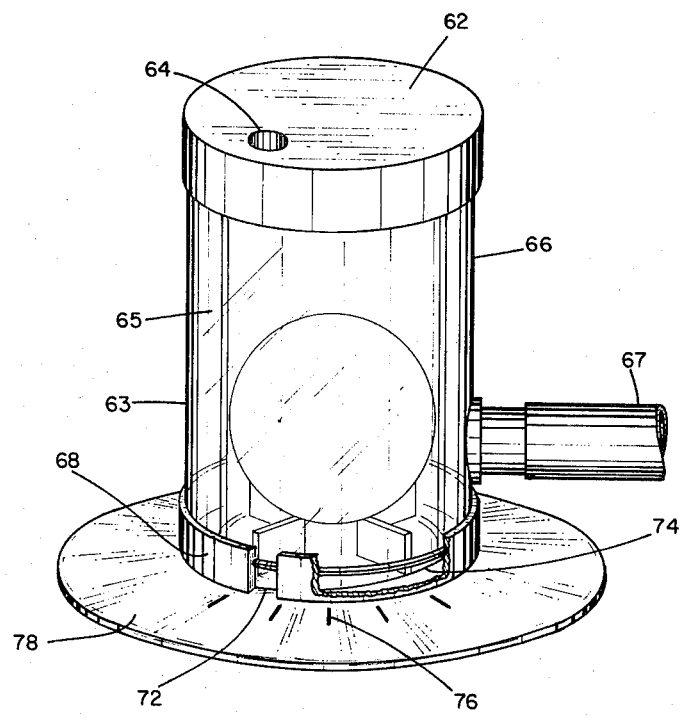
FIG. 12 is a perspective view of still another embodiment of the apparatus.

Although the device has been discussed herein as incorporating a rotatable cap for varying the by-pass port opening, an alternative embodiment is shown in FIG. 12, in which a by-pass port is located near the base or bottom, and wherein the spirometer body is rotated relative to the base. Specifically, the device includes a support in base 78 and a ring member 68, and incorporating a by-pass port 72. The ring member is partially broken away to expose and illustrate the lower helical surface for varying exercise difficulty. The ring member may conveniently be molded as an integral part of base 78 or otherwise secured thereto whereby the by-pass port opening is varied by rotating the spirometer body or base. Cap 62 includes a gas inlet port 64 for directing gas into the interior chamber. The outer spirometer body wall has a lower helical surface 74, similar to the upper helical surface of outer spirometer wall described previously. The cap may be secured on the spirometer body by convenient means and in sealing engagement to prevent substantial gas leakage around the cap. Gas exit pipe 67 covers a gas exit port communicating with passageway 65 between the inner and outer walls. A gas outlet port, not shown, communicates between the interior chamber and passageway 65. The device functions much like the previous embodiments, except that by-pass port 72 opening is increased or decreased as is exercise difficulty, by rotating ring member 68 relative to spirometer body 66. Thus, the helical surface causes more or less by-pass port opening exposure as the base is rotated. However, different sized orifice openings or an irregular surface for registering with the by-pass port may be used instead of a gradually sloping helical surface. A sealing means between ring member 68 and outer wall 63 and the base member will prevent undesirable gas leakage into passageway 65. Flow rate setting indicia 76 may be molded onto base 78 for conveniently showing exercise difficulty. A further variation of such an embodiment is to form the helical surface on the ring member, and the by-pass port on the outer wall, the device otherwise operating substantially as that shown.

The spirometer body walls are preferably constructed from a material, through which the ball can be readily reviewed. Any number of clear plastics may be suitable for that purpose. The device may also include additional or alternative means for detecting ball movement. For example, a microswitch or electrical contact type terminal could be provided as well as cooperating electronic means for counting the number of times the ball rises in the chamber, either partially or fully, as well as detecting time lapsed for holding the ball in a risen condition. The apparatus may include light detection means directed at the ball for counting elapsed ball rise time and number of rises. Other detection means such as an audible or higher frequency whistle may be installed for indicating a certain flow rate through the by-pass or gas inlet ports.

As for uses of the device, in addition to its independent function as a lung exerciser and spirometer, it may be combined with means for humidifying gas inspired by the user, or with a nebulizer, preferably secured between the device and the patient. Moreover, the apparatus may be used with a tracheotomy mask. A bacteria filter may also be incorporated for use with the device. Other uses, modification and embodiments of the invention within the purview disclosed herein will be evident to those skilled in the art.

I claim:

1. An incentive spirometer comprising a spirometer body having a lower wall, an outer wall and an inner wall concentrically oriented with respect to each other and separated by a passageway, said inner and outer walls extending generally normal to said lower wall, an interior chamber defined by said inner wall, and cover means overlying said passageway and interior chamber, gas inlet means for directing gas downwardly into said chamber, passage means for directing gas out of said chamber, across said inner wall and into said passageway, gas outlet means for directing gas out of said passageway, through said outer wall to the exterior thereof, by-pass control means movably secured on said body and cooperating with said outer wall, a closable by-pass gas opening defined by said by-pass control means cooperating with said outer wall through which gas from the exterior enters said passageway, and wherein the size of said opening is varied as said by-pass control means is moved on said body, and visual means associated with said interior chamber for indicating the rate of gas flow through said chamber.

2. The spirometer of claim 1 wherein said cover means and by-pass control means comprise a cap and said opening includes a by-pass port therein.

3. The spirometer of claim 2 wherein said inner and outer walls each have an upper annular surface, and wherein said cap overlies each said surface and covers said passageway and said chamber.

4. The spirometer of claim 2 wherein said outer wall sealingly engages said cap and includes a surface cooperating with said by-pass port, whereby movement of said cap varies said opening.

5. The spirometer of claim 4 wherein said surface cooperating with said by-pass port comprises a gradually slanting edge in registration with said port, whereby movement of said cap relative to said outer wall varies the alignment of said edge and said port and changes the size of said opening.

6. The spirometer of claim 2 wherein said inner and outer walls terminate in open upper ends, and said outer wall upper end includes means for varying the size of said by-pass port whereby said cap cooperating with said outer wall upper end varies the size of said by-pass port as said cap is rotated on said outer wall.

7. The spirometer of claim 6 wherein said outer wall upper end comprises a gradually slanted edge in registration with said by-pass port.

8. The spirometer of claim 6 or 7 wherein said inner wall upper end comprises a gradually slanted edge, includes means cooperating with wherein said cap and said inner wall upper edge to form said passage means, whereby movement of said cap varies the size of said passage means.

9. The spirometer of claim 1 wherein said by-pass control means comprises a member having a by-pass port therein rotably mounted on the lower end of said outer wall and cooperating therewith and wherein said outer wall lower end includes means for varying the size of said opening as said member is rotated on said outer wall.

10. The spirometer of claim 9 including a base member, and wherein said by-pass control means is secured thereto.

11. The spirometer of claim 1 and wherein said visual means comprises an article visible in said interior chamber and normally at rest in the bottom of said chamber and which is moved upwardly therein for indicating the rate of gas flow downwardly from said gas inlet means.

12. The spirometer of claim 1 wherein said passage means comprises a first outlet port communicating across said inner wall between said chamber and said passageway, and said gas outlet means comprises a second outlet port in said outer wall, communicating with said passageway.

13. The spirometer of claim 12, wherein said first outlet port comprises a walled channel forming in said cap and said inner wall includes a surface cooperating with said channel, whereby movement of said cap varies the size of said first outlet port.

14. The spirometer of claim 13 wherein said surface cooperating with said channel comprises a gradually slanting edge in registration with said channel, whereby movement of said cap relative to said inner wall varies the alignment of said channel and said edge and changes the size of the opening of said first outlet port.

15. The spirometer of claim 12 wherein said gas outlet means includes tubing connected to said second port and a mouthpiece connected to said tubing.

16. The spirometer of claim 12 wherein said gas inlet means includes a gas inlet port for directing gas into said chamber.

17. The spirometer of claim 16 wherein said opening of said by-pass control means communicates with said passageway.

18. The spirometer of claim 1 wherein said visual means comprises an article disposed in said chamber which is moved by gas passing through said chamber.

19. The spirometer of claim 18 wherein said article comprises a lightweight ball.

20. The spirometer of claim 1 wherein said cover means comprises a cap secured on said outer wall and overlying said passageway and said chamber.

21. The spirometer of claim 20 wherein said gas inlet means is formed in said cap.

* * * * *